United States Patent
Joseph

(10) Patent No.: US 11,369,667 B2
(45) Date of Patent: *Jun. 28, 2022

(54) **COLLAGENASE *CLOSTRIDIUM HISTOLYTICUM* FOR TREATMENT OF BLADDER DYSFUNCTION**

(71) Applicant: InnoMed Technologies, Inc., Encino, CA (US)

(72) Inventor: John Joseph, Westlake Village, CA (US)

(73) Assignee: InnoMed Technologies, Inc., Encino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/516,631

(22) Filed: Nov. 1, 2021

(65) Prior Publication Data

US 2022/0047689 A1 Feb. 17, 2022

Related U.S. Application Data

(63) Continuation-in-part of application No. 17/066,462, filed on Oct. 8, 2020, now Pat. No. 11,253,575.

(60) Provisional application No. 63/015,166, filed on Apr. 24, 2020.

(51) Int. Cl.
| | | |
|---|---|---|
| *A61P 13/10* | (2006.01) | |
| *A61K 38/48* | (2006.01) | |
| *A61K 9/00* | (2006.01) | |

(52) U.S. Cl.
CPC ........ *A61K 38/4886* (2013.01); *A61K 9/0019* (2013.01); *A61P 13/10* (2018.01)

(58) Field of Classification Search
None
See application file for complete search history.

(56) References Cited

U.S. PATENT DOCUMENTS 11,083,781 B1 * 8/2021 Joseph .................... A61P 11/00
2021/0330764 A1 * 10/2021 Joseph .................... A61K 45/06

OTHER PUBLICATIONS

Rabasseda X. Annual Meeting of the American Urological Association. Drugs of the Future 38(6)411-422, Jun. 2013. (Year: 2013).*
Balzarro M. et al. OnabotulinumtoxinA Detrusor Injection Improves Female Sexual Function in Women with Overactive Bladder Wet Syndrome European J of Obstetrics & Gynecology and Reproductive Biology 225:228-231, 2018. (Year: 2018).*

* cited by examiner

*Primary Examiner* — Ralph J Gitomer
(74) *Attorney, Agent, or Firm* — Entralta; James F Fleming; Peter D Weinstein

(57) ABSTRACT

Collagenase *Clostridium histolyticum* (EN3835) is a proteinase that can hydrolyze the triple-helical region of collagen under physiological conditions. EN3835 targets the collagenase structural matrix at the site of injection and does not require systemic exposure. Embodiments include methods of lysing subdermal and submucosal collagen to treat various conditions such as bladder dysfunction, esophageal stenosis, benign prostatic hyperplasia, tracheal stenosis, subglottic stenosis and scleroderma.

20 Claims, No Drawings

COLLAGENASE *CLOSTRIDIUM HISTOLYTICUM* FOR TREATMENT OF BLADDER DYSFUNCTION

RELATED APPLICATIONS

This application is a Continuation in Part of U.S. patent application Ser. No. 17/066,462 filed on Oct. 9, 2020 which claims priority to U.S. provisional patent application Ser. No. 63/015,166 filed on Apr. 24, 2020. The contents of the aforementioned applications are incorporated herein by reference.

FIELD OF THE INVENTION

The invention relates to enzymes that dismantle collagen and methods of using them, and more specifically, it relates to the use of Collagenase *Clostridium histolyticum* (CCH) for treatment of bladder dysfunction, esophageal stenosis, tracheal stenosis and benign prostatic hyperplasia.

BACKGROUND

Ventilators are commonly used in hospital settings to assist patients with breathing. A ventilator provides mechanical ventilation by moving breathable air into and out of the lungs to deliver breaths to a patient who is physically unable to breathe or is breathing insufficiently. For example, patients with acute respiratory distress syndrome may require ventilation assisted breathing for extended periods of time. The syndrome entails widespread inflammation in the lungs which impairs the ability of the lungs to absorb oxygen and expel carbon dioxide.

Tracheal intubation refers to placing a flexible plastic tube into the trachea (i.e., windpipe) to maintain an open airway. It is often used with mechanical ventilation in critically injured, ill or anesthetized patients. It facilitates ventilation of the lungs and can prevent the possibility of asphyxiation or airway obstruction.

The most widely used route of tracheal intubation is orotracheal, wherein an endotracheal tube is passed through the mouth and vocal apparatus into the trachea. In a nasotracheal procedure, an endotracheal tube is passed through the nose and vocal apparatus into the trachea. Other methods of intubation involve surgery and include the cricothyrotomy and the tracheotomy, used primarily in situations where a prolonged need for airway support is anticipated.

Prolonged placement of an endotracheal tube or tracheostomy can lead to tracheal stenosis. Tracheal stenosis is a narrowing of the trachea due to the formation of scar tissue or malformation of the cartilage in the trachea. While mild narrowing in the trachea can be innocuous, a significant narrowing of the airway can lead to serious complications. Other causes of tracheal stenosis include inflammatory bowel disease, collagen vascular disease, congenital malformations, trauma, inhalation burns, radiation therapy, infection, inflammatory diseases (e.g. sarcoidosis or amyloidosis) and cancer.

Stenosis can also be caused by scarring from autoimmune disease. Scleroderma is a chronic autoimmune disease in which normal tissue is replaced with thick tissue with extra collagen. Although it most often affects the skin, scleroderma also can affect many other parts of the body. For example, it can cause stenosis of the esophagus. Strictures of the esophagus can require stretching. Patients are often forced to use a feeding tube placed through the abdominal wall.

The subglottis is the area just beneath the vocal folds. Subglottic stenosis is a narrowing of the subglottis. This narrowing is most often made of scar tissue. Subglottic stenosis is most often seen in children who have undergone prolonged intubation on a respirator. They may be required to get a permanent tracheotomy (i.e., a hole cut in throat) for direct access to the trachea. The surgery often creates significant scarring and can present other complications.

Conventional treatments for tracheal and subglottic stenosis are often inadequate. If the area of stenosis is small, placing a stent, dilating your trachea with a balloon, or removing some of the scar tissue with a laser can be options. During these procedures, steroids can be injected into the tissue in the trachea to help minimize swelling. Another option is tracheal resection, which requires surgery. This procedure is typically used only when endoscopic treatments have failed, or tracheal stenosis is too severe for endoscopic procedures. During this procedure, a portion of the trachea is surgically removed and repaired with skin or cheek tissue.

Benign prostatic hyperplasia (BPH) is similar in that it can be characterized by an growth of a dense collagen network. As the prostate issue enlarges, the surrounding capsule prevents it from radially expanding leading to urethral compression. Advanced stages of BPH can cause serious problems such as urinary tract infections, bladder and kidney damage, including bladder stones, incontinence and most seriously, gross hematuria and renal failure due to obstructive uropathy. Conventional strategies for treating BPH include invasive surgery. Surgical procedures such as transurethral incision of the prostate (TUIP), transurethral resection of the prostate (TURP), and open prostatectomy present risks of impotence, incontinence and the need for re-treatment. Few treatments are without any adverse consequences. With conventional treatments, patients and providers face a balancing act between the benefits and demerits of the treatment. Non-surgical options offer additional options but also have limitations.

Non-surgical options include alpha blocker therapy, finasteride therapy and balloon dilation. Medications in the class known as 5-alpha-reductase inhibitors can lower production of the hormone dihydrotestoterone, which is responsible for growth of the acinar glands of the prostate. They include Finasteride and dutasteride. The inhibitors can prevent progression of growth of the prostate and sometimes reduce the size of the prostate. Another class of drugs for treating BPH is the alpha-1-adrenergic receptor blockers (alpha blockers), which act by relaxing the smooth muscle of the prostate and bladder neck to improve urine flow and reduce bladder outlet obstruction. Studies demonstrate that these therapies are often ineffective, particularly in advanced cases of BPH.

Accordingly, there is a need for improved methods to treat BPH, tracheal and subglottic stenosis as well as strictures. Such methods should target collagen or scar tissue and have other applications. The methods should be safe, effective and minimally invasive.

SUMMARY OF THE INVENTION

The inventions described and claimed herein have many attributes and embodiments including, but not limited to, those set forth or described or referenced in this brief summary. The inventions described and claimed herein are not limited to, or by, the features or embodiments identified in this summary, which is included for purposes of illustration only and not restriction.

Embodiments include the proteinase collagenase *Clostridium histolyticum* ("EN3835") and similar compounds for therapeutic use. Collagenase *Clostridium histolyticum* is composed of the two collagenases: clostridial class I Collagenase (AUX-I) and Clostridial class II collagenase (AUX-II). Both collagenases are secreted bacterial proteins isolated from clostridium histolyticum.

Collagenase *Clostridium histolyticum* can hydrolyze the triple-helical region of collagen under physiological conditions. It targets the collagenase structural matrix at the site of injection and does not require systemic exposure. Embodiments include methods of lysing subdermal and/or submucosal collagen to treat various conditions such as tracheal stenosis, subglottic stenosis and scleroderma.

In embodiments, the present disclosure provides for a method of reducing localized collagen tissue in a patient comprising injection of collagenase *Clostridium histolyticum* (EN3835) at or near the localized collagen tissue. The localized collagen tissue can be scar tissue and identified as subglottic or tracheal stenosis. The localized collagen tissue can be the result of an autoimmune disease such as scleroderma. The localized collagen tissue can be the result of prostate growth and be characterized as prostatic hyperplasia.

Additional embodiments include methods of treating a patient with tracheal stenosis, subglottic stenosis or esophageal stricture that includes injecting collagenase *Clostridium histolyticum* (EN3835) at or near the stenotic region. A treatment regime can include multiple injections per session. The injections are preferably at different sites at or near the localized collagen. In an embodiment, a total of 0.01 mg to 0.5 mg of collagenase *Clostridium histolyticum* in solution is injected per session. In another embodiment, a total of 0.02 mg to 0.05 mg of collagenase *Clostridium histolyticum* in solution is injected per session. A treatment regime can be altered and/or extended based on results such as the size of the localized and signs/symptoms. Also described is a kit for reducing scar tissue in a patient. The kit can include collagenase *Clostridium histolyticum* (EN3835) and an accufill syringe.

Additional embodiments include methods of treating or preventing benign prostatic hyperplasia (BPH) that includes injecting collagenase *Clostridium histolyticum* (EN3835) at or near prostate tissue. Also described is a kit for reducing/removing prostate tissue in a patient. The kit can include collagenase *Clostridium histolyticum* (EN3835) and an accufill syringe.

Applicant has recognized that levels of collagen in the detrusor muscle of the bladder can increase with age leading to bladder dysfunction. Accordingly, embodiments include methods of treating bladder dysfunction using collagenase *Clostridium histolyticum* (CCH). The bladder dysfunction can be urinary incontinence and/or urinary retention.

Additional embodiments include methods of treating bladder dysfunction using collagenase *Clostridium histolyticum* (CCH) that is injected at or near the detrusor muscle of the bladder.

Additional embodiments include methods of treating bladder dysfunction using collagenase *Clostridium histolyticum* (CCH) that is injected at or near the bladder including the wall of the bladder.

Additional embodiments include methods of treating bladder obstruction using collagenase *Clostridium histolyticum* (CCH) that is injected at or near the prostate.

Embodiments also include a method of treating bladder dysfunction in a patient comprising steps of (a) identifying a patient with signs and/or symptoms of bladder dysfunction, (b) injecting an effective amount of collagenase from *Clostridium histolyticum* at a first plurality of sites at or near the bladder and/or the detrusor muscle of the bladder, (c) monitoring signs and/or symptoms of bladder dysfunction, (d) injecting an effective amount of collagenase at a second plurality of sites at or near the bladder and/or the detrusor muscle of the bladder and (e) repeating steps c) and d) until the signs and/or symptoms of bladder dysfunction subside.

The treatment of bladder dysfunction can include multiple injections at a plurality of sites at the bladder wall and/or the detrusor muscle. Each injection can be a volume of about 0.2 ml or less. The total amount of CCH used in the treatment can be 0.01 mg to 0.5 mg. In another embodiment, the total amount of CCH is 0.02 mg to 0.05 mg. The treatment can include an additional step of endoscopic dilation. The collagenase can be comprised of equal amounts of Clostridial class I collagenase (AUX-I) and Clostridial class II collagenase (AUX-II) and be injected using a syringe with a rack and pinion component.

Definitions

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can be in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

The term "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. An active agent can be a primary active agent, or in other words, the component(s) of a composition to which the whole or part of the effect of the composition is attributed. An active agent can be a secondary agent, or in other words, the component(s) of a composition to which an additional part and/or other effect of the composition is attributed.

The term "Accufill syringe" refers to a syringe with a rack and pinion component. This is in contrast to a conventional syringe that includes a plunger and a barrel. An Accufill syringe can be preferred for injection because scar tissue is dense and higher pressure may be necessary to inject the drug product. The design is also conducive to continuous flow with precise delivery. The rack and pinion assembly has two components (i.e. a toothed rack and a pinion gear).

The term "*Clostridium histolyticum*" refers to a species of bacteria found in feces and the soil. It is a motile, gram-positive, aerotolerant anaerobe. It is pathogenic in many species, including guinea pigs, mice, and rabbits, and humans. It has been shown to cause gas gangrene, often in association with other bacteria species.

The term "Dupuytren's contracture" refers a progressive disease of the hand wherein a collagen-containing cord forms in the palm and finger. The cord thickens, shortens, and may pull the finger toward the palm.

The term "Edematous fibrosclerotic panniculopathy" or "EFP" has been defined as a local metabolic disorder of subcutaneous tissues that results in an alteration of skin topography. The condition manifests as dimpled skin, described as an orange-peel, cottage cheese, or mattress texture, particularly in the gluteal-femoral region. EFP is caused by herniation of subcutaneous fat lobules through the dermohypodermal junction. This creates an uneven surface with dimpling.

The term "esophageal stricture" refers to the abnormal narrowing of the esophageal lumen. It often presents as dysphagia commonly described by patients as difficulty swallowing. It is a serious sequela to many different disease processes and underlying etiologies.

The term "Peyronie's disease" refers to a connective tissue disorder involving the growth of fibrous plaques in the soft tissue of the penis. Specifically, scar tissue forms in the tunica albuginea, the thick sheath of tissue surrounding the corpora cavernosa, causing pain, abnormal curvature, erectile dysfunction, indentation, loss of girth and shortening.

The term "Benign prostatic hyperplasia," "benign prostatic hypertrophy" or "BPH" refers a non-cancerous condition resulting from enlargement of the prostate gland as a consequence of the natural progression of prostate growth with age. Enlargement of the prostate can be a result of increased prostate cell proliferation, or an increase in prostate cell size. An enlarged prostate gland can cause uncomfortable urinary symptoms, such as blocking the flow of urine out of the bladder. It can also cause bladder, urinary tract or kidney problems. Conventional treatments include transurethral resection and other methods to surgically remove the prostate or remove a portion.

"Adhesive capsulitis," also known as frozen shoulder, refers to a condition associated with shoulder pain and stiffness caused by inflammation and scarring. There is a loss of the ability to move the shoulder, both voluntarily and by others, in multiple directions. The cause in most cases is unknown. The condition can also occur after injury or surgery to the shoulder. Risk factors include diabetes and thyroid disease. The underlying mechanism involves Inflammation and scarring.

"Edematous fibrosclerotic panniculopathy" or "EFP" refers to a condition associated with thickening and contraction of collagen-rich subdermal septae.

The term "scar" or "scar tissue" refers to an area of fibrous tissue that replaces normal skin after an injury. Scars result from the biological process of wound repair in the skin, as well as in other organs and tissues of the body. Thus, scarring is a natural part of the healing process. Scar tissue is composed of the same protein (collagen) as the tissue that it replaces, but the fiber composition of the protein is different. Instead of a random basketweave formation of the collagen fibers as in normal tissue, the collagen cross-links and forms a pronounced alignment in a single direction in fibrosis.

The term "esophageal stricture" or "esophageal stenosis" refers to an abnormal tightening of the esophagus. Esophageal strictures can limit or block food and liquid traveling from the throat to the stomach. This can make swallowing difficult because of the smaller area. Other symptoms include a bitter or acid taste in the mouth, choking, coughing, shortness of breath, frequent burping and hiccups. GERD is the most common cause of strictures, but there are other causes such as esophagitis, cancer, traumatic ingestion of agents (e.g., caustic agents) and radiation treatment. Conventional treatments for esophageal stricture include a dilation procedure to physically widen the esophagus and reduce symptoms.

The term "gastroesophageal reflux disease" or "GERD" refers to a digestive disorder in which stomach acid or bile irritates the lining of the esophagus. It can affect the ring of muscle between the esophagus and stomach (i.e., the lower esophageal sphincter or LES). Common symptoms include heartburn and acid indigestion. Complications of GERD include esophagitis, esophageal stricture and Barrett's esophagus.

The term "bladder obstruction" refers to a blockage at the base or neck of the bladder. Such a blockage can reduce or stop the flow of urine into the urethra. Bladder obstruction is common in older men and often linked to enlarged prostate.

The term "bladder dysfunction" refers to problems with urination. Problems include urgency of urination, frequency of urination, ability to "hold" urine during the day or night, urinary incontinence, infrequent voiding (not urinating often), constipation and other diagnoses.

The term "urinary incontinence" or "involuntary urination" refers to any uncontrolled leakage of urine. It is a common and distressing problem which can have a large impact on quality of life. It has been identified as an important issue in geriatric health care. The term enuresis is often used to refer to urinary incontinence primarily in children, such as nocturnal enuresis (i.e., bed wetting). There are four main types of incontinence: (a) urge incontinence due to an overactive bladder, (b) stress incontinence due a poorly functioning urethral sphincter muscle (intrinsic sphincter deficiency) or to hypermobility of the bladder neck or urethra, (c) overflow incontinence due to either poor bladder contraction or blockage of the urethra and (d) mixed incontinence involving features of one or more types. Conventional treatments for urinary incontinence include pelvic floor muscle training, bladder training, surgery and electrical stimulation.

The term "urinary retention" refers to an inability to completely empty the bladder. Onset can be sudden or gradual. When of sudden onset, symptoms can include an inability to urinate and lower abdominal pain. When of gradual onset, symptoms can include loss of bladder control, mild lower abdominal pain and a weak urine stream. Those with long-term problems are at risk of urinary tract infections. Causes or urinary retention include blockage of the urethra, nerve problems, certain medications and weak bladder muscles. Blockage can be caused by benign prostatic hyperplasia (BPH), urethral strictures, bladder stones, a cystocele, constipation or tumors. Nerve problems can occur from diabetes, trauma, spinal cord problems, stroke, or heavy metal poisoning. Medications that can cause problems include anticholinergics, antihistamines, tricyclic antidepressants, decongestants, cyclobenzaprine, diazepam, non-steroidal anti-inflammatory drugs (NSAID), amphetamines and opioids. Diagnosis is typically based on measuring the amount of urine in the bladder after urinating. Conventional methods of treatment typically include the use of a catheter either through the urethra or lower abdomen. Other treatments include medication to decrease the size of the prostate, urethral dilation, a urethral stent, or surgery.

The term "detrusor muscle" refers to smooth muscle found in the wall of the bladder. The detrusor muscle remains relaxed to allow the bladder to store urine and contracts during urination to release urine. Related are the urethral sphincter muscles which envelop the urethra to control the flow of urine when they contract. As subjects age, the bladder appears to have a thickened muscularis layer similar to that seen after obstruction. For example, aging male rats have been shown to have an increased frequency of micturition and much higher voiding pressure compared with young rats. A urodynamic study in men and women demonstrated that, in both sexes, postvoid residual volume increased with age, whereas peak flow rate and bladder capacity decreased; there was no correlation between age and maximum detrusor pressure or detrusor pressure at peak flow rate. The key underlying mechanisms of voiding dysfunction in the elderly appear to include deterioration of detrusor muscle function, bladder wall fibrosis and increased sensitivity to neurotransmitters (especially norepinephrine).

The term "subject" or "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e. arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e. reversing the pathology and/or symptomatology) such as decreasing the severity of disease.

Other technical terms used herein have their ordinary meaning in the art that they are used, as exemplified by a variety of technical dictionaries. The particular values and configurations discussed in these non-limiting examples can be varied and are cited merely to illustrate at least one embodiment and are not intended to limit the scope thereof.

DESCRIPTION OF EMBODIMENTS

It is to be understood that both the foregoing general description and the following detailed description are exemplary and explanatory and are intended to provide further explanation of the subject technology as claimed. Additional features and advantages of the subject technology are set forth in the description below, and in part will be apparent from the description, or may be learned by practice of the subject technology. The advantages of the subject technology will be realized and attained by the structure particularly pointed out in the written description and claims hereof.

Collagenase *Clostridium histolyticum* ("EN3835") is a combination of two enzymes produced by the bacterium *Clostridium histolyticum* that dismantles collagen. Specifically, it is composed of two collagenases that are present in an approximately equal mass ratio, Clostridial class I collagenase (AUX-I) and Clostridial class II collagenase (AUX-II). Both collagenases are secreted bacterial proteins isolated from *Clostridium histolyticum*.

Clostridial class I collagenase (AUX-I) is a single polypeptide chain of approximately 1000 amino acids with a molecular weight of 114 kDa. Collagenase AUX-I is functionally classified as Class I collagenase. Clostridial class II collagenase (AUX-II) is also a single polypeptide chain of approximately 1000 amino acids with a molecular weight of 113 kDa. Collagenase AUX-II functionally belongs to Class II collagenase from *C histolyticum*.

Both collagenases digest collagen by hydrolyzing the triple helical region of collagen under physiological conditions. Each collagenase has different specificity; Class I enzymes first hydrolyze loci near the amino and carboxy termini of the triple helical domains of the collagen molecule and Class II collagenases make their initial cleavage near the interior of the molecule. While both collagenases are immunologically distinct and have different specificities, together they work synergistically, and provide a very broad hydrolyzing reactivity toward collagen.

The differences between the two collagenase classes result in improved activity against collagen when they are combined compared with the activity seen with either class acting alone. The fixed-ratio of AUX-I and AUX-II represented in EN3835 drug product falls within the range of effective ratios for which improved rate and completeness of digestion of either soluble or intact interstitial collagen has been demonstrated.

EN3835 has therapeutic uses because of its ability to dismantle collagen. Its pharmacologic activity involves selective lysis of collagen at the site of injection. EN3835's therapeutic activity is thus localized and it does not require systemic exposure. It is used to treat Dupuytren's contracture, a condition where the fingers bend towards the palm and cannot be fully straightened. It is also used to treat Peyronie's disease, a connective tissue disorder involving the growth of fibrous plaques in the soft tissue of the penis.

Studies indicate that when EN3835 is injected into tissues composed primarily of dense fibrous connective tissue arranged in larger fibrils (e.g. tunica albuginea, Peyronie's plaque, tendon, pericardium, or Dupuytren's cord); either in vitro or in vivo, lysis is focal, well circumscribed and primarily confined to tissue directly adjacent to the injection site. In contrast, lysis following injection into loosely arrayed fibrous connective tissue composed of smaller fibrils (corpus cavernosum or subcutaneous tissue) is more diffuse. These findings support the potential use of of EN3835 in the treatment of localized fibrotic conditions such as BPH, tracheal stenosis, subglottic stenosis and scleroderma.

Methods of Treatment Using EN3835

A scar is an area of fibrous tissue that replaces normal skin after an injury. Scars result from the biological process of wound repair in the skin, as well as in other organs and tissues of the body. Thus, scarring is a natural part of the healing process. With the exception of very minor lesions, every wound (e.g., after accident, disease, or surgery) results in some degree of scarring. An exception to this are animals with complete regeneration, which regrow tissue without scar formation.

Scar tissue is composed of the same protein (collagen) as the tissue that it replaces, but the fiber composition of the protein is different; instead of a random basketweave formation of the collagen fibers found in normal tissue, in fibrosis the collagen cross-links and forms a pronounced alignment in a single direction. This collagen scar tissue alignment is usually of inferior functional quality to the normal collagen randomised alignment.

Applicants have found that the use of EN3835 for administration by injection into localized deposits of pathologic collagen to result in therapeutically effective lysis and removal of the collagen. Further, studies have demonstrated that EN3835 has limited or no quantifiable systemic exposure with no systemic toxicity following local administration. Local findings were restricted to the site of injection and the draining lymph node and were qualitatively similar across species and sexes, with almost complete recovery of the gross findings following the cessation of treatment, with ongoing healing processes (including injection site fibrosis). Following intravenous (IV) bolus administration of the commercial drug product, the primary target organ was the liver and a clear systemic no observed effect level (NOEL) and adequate margins (~2.5×human equivalent dose [HED] on a body surface area basis) were established to account for inadvertent administration of a 10,000 U clinical dose into the systemic circulation. Local injection site findings were also observed, with evidence of a dose response for some findings and complete/partial reversibility by the end of the recovery phase. Anti-EN3835 antibodies were raised in almost all animals after local or IV administration; although no evidence for antibody-mediated adverse effects were observed.

Esophageal Stricture/Stenosis

Strictures can form after esophageal surgery and other treatments such as laser therapy or photodynamic therapy. As the area heals, a scar forms, causing the tissue to pull and tighten, leading to difficulty in swallowing. Strictures can be diagnosed with an X-ray (i.e., barium study of the esophagus), by a computerized tomography scan, a biopsy or by endoscopy.

One embodiment is a method of treating esophageal stricture using CCH. The CCH is injected at or near the site of the stricture. The tissue that forms the stricture is effectively dissolved by the protease activity of the CCH. Injections can be repeated as needed. For example, a patient can receive three doses per treatment cycle. The treatment cycle can be repeated two or more times (e.g., at six weeks and three months after the first injection) based on the discretion of the health care provider. The dimensions of the stenotic region can be measured and monitored during the course of treatment. In one embodiment, CCH is used in conjunction with a dilation procedure to physically widen the esophagus.

Urinary Retention

Urinary retention can be caused by bladder outlet obstruction and an ineffective detrusor muscle. For example, benign prostatic hyperplasia (BPH) is a common disease in aged men and is often associated with prostate enlargement and lower urinary tract symptoms. Bladder outlet obstruction has long been considered a key factor in the mechanism through which BPH causes urinary retention. Accordingly, treatments are often directed at relieving the obstruction. Applicant proposes another cause of urinary retention is increased levels of collagen, specifically in the detrusor muscle of the bladder and nearby muscle tissue. Bladder dysfunction can develop with age as collagen levels increase and/or collagen fibers lose their elasticity. In bladders that become noncompliant, there can be interference with the ability of the collagen fibers to elastically and reversibly alter their tortuosity. This will can reduce total bladder capacity and cause urinary retention as well as urinary incontinence.

Bladder outlet obstruction can induce morphophysiological changes in the bladder that can cause bladder dysfunction, including detrusor overactivity (DO), detrusor underactivity, and decreased compliance. Men with bladder outlet obstruction due to BPH (BOO/BPH) may develop detrusor hypertrophy and hyperplasia and accumulation of connective tissue within the muscle bundles. Studies including men with BOO/BPH have shown increased collagen content in the bladder wall and the detrusor muscle. It has also been suggested that the magnitude of detrusor collagen deposition is associated with the severity of lower urinary tract symptoms in men with BOO/BPH.

In one embodiment, CCH is injected at or near the bladder wall and/or the site of the detrusor muscle. Excess collagen can be effectively dissolved by the protease activity of the CCH. Injections can be repeated as needed. For example, a patient can receive three doses per treatment cycle. The treatment cycle can be repeated two or more times (e.g., at six weeks and three months after the first injection) based on the discretion of the health care provider. The bladder compliance and capacity can be measured and monitored during the course of treatment. In one embodiment, CCH is used in conjunction with one or more conventional treatments including physical dilation and medications.

Urinary Incontinence

As described above, bladder outlet obstruction can cause morphophysiological changes in the bladder that can cause bladder dysfunction. Urinary incontinence (i.e., the inability to effectively empty the bladder) is a common dysfunction. Patients may present detrusor hypertrophy and hyperplasia and accumulation of connective tissue within the muscle bundles. Without being bound by theory, Applicant proposes that urinary incontinence can be caused by increased levels of collagen in the wall of the bladder and/or the detrusor muscle. Applicant proposes that the extent of collagen deposition is associated with the severity of urinary incontinence.

In another embodiment, CCH is injected at or near the wall of the bladder and/or the site of the detrusor muscle to treat urinary incontinence. Excess collagen is dissolved by the protease activity of the CCH as described above. The bladder compliance and capacity can be measured and monitored during the course of treatment. In one embodiment, CCH is used in conjunction with one or more conventional treatments.

Tracheal Stenosis

Prolonged placement of an endotracheal tube or tracheostomy can lead to tracheal stenosis. Tracheal stenosis is a narrowing of the trachea due to the formation of scar tissue or malformation of the cartilage in the trachea. In one embodiment, EN3835 is injected at or near the site of the stenosis. The tissue that forms the stenosis is effectively dissolved by the protease activity of the EN3835. Injections can be repeated as needed. For example, a patient can receive three doses per treatment cycle. The treatment cycle can be repeated two or more times (e.g. at 6 weeks and 3 months after the first injection) based on the discretion of the health care provider. The dimensions of the stenotic region can be measured and monitored during the course of treatment.

Subglottic Stenosis

The subglottis is the area just beneath the vocal folds. EN3835 can be used in the same manner to target tissue causing subglottic stenosis. As described above, the tissue that forms the stenosis is effectively dissolved by the protease activity of the EN3835. Injections can be repeated as needed. The dimensions of the stenotic region can be measured and monitored during the course of treatment Scleroderma Stenosis can also be caused by scarring from autoimmune disease. Scleroderma is a chronic autoimmune disease in which normal tissue is replaced with thick tissue with extra collagen. Although it most often affects the skin, scleroderma also can affect many other parts of the body such as the esophagus. The same approach can be used for esophageal stricture. The tissue that forms the stenosis is effectively dissolved by the protease activity of the EN3835. Injections can be repeated as needed.

Benign Prostatic Hyperplasia

Another aspect of the invention is a method of treating BPH using EN3835. It is estimated that 60% of American men in their sixties have some symptoms of BPH and that the condition affects more than 90% of men in their seventies and eighties. Due to the aging of the population, the prevalence is expected to increase substantially.

The prostate is comprised of a functional secretory epithelium, a basal epithelium, and a supporting stroma comprised of structural elements, and a spectrum of cell types that includes smooth muscle cells, fibroblasts, and inflammatory cells. The prostate is supported by a highly structured network of collagen fibers. This network of fibers varies in normal and diseased states. In benign prostatic hyperplasia, the collagen network is dense, with an increased number of fibers. As the prostate enlarges, the surrounding capsule prevents it from radially expanding, potentially resulting in urethral compression.

With age, the prostate exhibits glandular enlargement, increased smooth muscle tone and decreased compliance secondary to altered collagen deposition. These changes can lead to altered urinary symptoms due to outlet obstruction. Severe BPH can cause serious problems over time, such as urinary tract infections, and bladder or kidney damage.

Applicants have found that the use of EN3835 for administration by injection into localized deposits of pathologic collagen result in lysis and removal of the collagen. EN3835 can be administered at or near the prostate by injection. Thereafter, the size of the tissue can be monitored. As described above, multiple doses of EN3835 can be administered based on the course of treatment and the needs of the patient.

This method has minimal side-effects, particularly compared to conventional treatments. As stated above, studies have demonstrated that EN3835 has limited or no quantifiable systemic exposure with no systemic toxicity following local administration.

Utility and Administration

For use as treatment of human and animal subjects, the compounds of the invention can be formulated as pharmaceutical or veterinary compositions. Depending on the subject to be treated, the mode of administration, and the type of treatment desired (e.g., prevention, prophylaxis, or therapy) the compounds are formulated in ways consonant with these parameters. A summary of such techniques is found in *Remington: The Science and Practice of Pharmacy, 21" Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

In one embodiment, the EN3835 drug product is stored and shipped in sterile lyophile, e.g. 3 mL clear Type I glass vial with a chlorobutyl rubber stopper (no latex) and capped with an overseal and blue tear-off cap or a 2-mL clear Type I glass vial with a chlorobutyl rubber stopper (no latex) and capped with an overseal and red tear-off cap. The cake is reconstituted before subject use with single-use sterile diluent (2 mM calcium chloride and 154 mM sodium chloride solution in water for injection or 2 mM calcium chloride and 103 mM sodium chloride in water for injection).

In one embodiment, sterile diluent for reconstitution of EN3835 is provided in a 5 mL or a 2 mL clear Type I glass vial with a chlorobutyl rubber stopper (no latex) and capped with an overseal and blue tear-off cap. A suitable sterile buffered diluent can include 10 mM Tris, 2 mM CaCl, and 154 mM NaCl.

Certain embodiments of the invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Administration

A pharmaceutical composition comprising EN3835 in accordance with the present disclosure can be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions can include suitable solid or gel phase carriers or excipients. Exemplary carriers or excipients include calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases it will be preferable to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life or effectiveness of the therapeutic agents.

The EN3835 can be incorporated into a pharmaceutical composition suitable for parenteral administration. Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05%>polysorbate-80 (optimally 0.005-0.01%). Additional surfactants include but are not limited to polysorbate 20 and BRIJ surfactants.

The EN3835 preparation can be lyophilized and stored as sterile powders, preferably under vacuum, and then reconstituted in bacteriostatic water (containing, for example, benzyl alcohol preservative) or in sterile water prior to injection. Pharmaceutical compositions can be formulated for parenteral administration by injection e.g., by bolus injection or continuous infusion.

The therapeutic agents in the pharmaceutical compositions can be formulated in a "therapeutically effective amount" or a "prophylactically effective amount". A "therapeutically effective amount" refers to an amount effective, at dosages and for periods of time necessary, to achieve the desired therapeutic result. A therapeutically effective amount of the protease (i.e. EN3835) may vary depending on the condition to be treated, the severity and course of the condition, the mode of administration, whether the agent is administered for preventive or therapeutic purposes, the bioavailability of the particular agent, the ability of the agent to elicit a desired response in the individual, previous therapy, the age, weight and sex of the patient, the patient's clinical history and response to the agent, discretion of the attending physician, etc. A therapeutically effective amount is also one in which any toxic or detrimental effects is not outweighed by the therapeutically beneficial effects. A "prophylactically effective amount" refers to an amount effective, at dosages and for periods of time necessary, to achieve the desired prophylactic result.

The solution containing EN3835 is suitably administered to the patient at one time or over a series of treatments and may be administered to the patient at any time from diagnosis onwards. The solution can be administered as the sole treatment or in conjunction with other drugs or therapies useful in treating the condition in question.

As a general proposition, a therapeutically effective amount or prophylactically effective amount of EN3835 will be administered in a range from about 1 ng/kg body weight to about 100 mg/kg body weight whether by one or more administrations. In a particular embodiment, the agent is administered in the range of from about 1 ng/kg body weight to about 10 mg/kg body weight, about 1 ng/kg body weight to about 1 mg/kg body weight, about 1 ng/kg body weight to about 100 g/kg body weight, about 1 ng/kg body weight to about 10 g/kg body weight, about 1 ng/kg body weight/day to about 1 g/kg body weight, about 1 ng/kg body weight to about 100 ng/kg body weight, about 1 ng/kg body weight to about 10 ng/kg body weight, about 10 ng/kg body weight to about 100 mg/kg body weight, about 10 ng/kg body weight to about 10 mg/kg body weight, about 10 ng/kg body weight to about 1 mg/kg body weight, about 10 ng/kg body weight/ to about 100 g/kg body weight, about 10 ng/kg body weight to about 10 mg/kg body weight, about 10 ng/kg body weight to about 1 mg/kg body weight, 10 ng/kg body weight to about 100 ng/kg body weight/, about 100 ng/kg body weight to about 100 mg/kg body weight, about 100 ng/kg body weight to about 10 mg/kg body weight, about 100 ng/kg body weight to about 1 mg/kg body weight, about 100 ng/kg body weight to about 100 mg/kg body weight, about 100 ng/kg body weight to about 10 mg/kg body weight, about 100 ng/kg body weight to about 1 mg/kg body weight, about 1 mg/kg body weight to about 100 mg/kg body weight, about 1 mg/kg body weight to about 10 mg/kg body weight/day, about 1 mg/kg body weight to about 1 mg/kg body weight, about 1 mg/kg body weight to about 100 mg/kg body weight, about 1 mg /kg body weight to about 10 mg/kg body weight, about 10 mg/kg body weight to about 100 mg/kg body weight, about 10 mg/kg body weight to about 10 mg/kg body weight, about 10 mg/kg body weight to about 1 mg/kg body weight/day, about 10 mg/kg body weight to about 100 mg/kg body weight, about 100 mg/kg body weight/day to about 100 mg/kg body weight, about 100 mg/kg body weight/day to about 10 mg/kg body weight, about 100 mg/kg body weight/day to about 1 mg/kg body weight, about 1 mg/kg body weight to about 100 mg/kg body weight, about 1 mg/kg body weight to about 10 mg/kg body weight, about 10 mg/kg body weight to about 100 mg/kg body weight/day.

In other embodiments, EN3835 is administered in the range of about 10 ng to about 100 ng per individual administration, about 10 ng to about 1 g per individual administration, about 10 ng to about 10 g per individual administration, about 10 ng to about 100 mg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 mg per individual administration, about 100 ng to about 10 mg per individual administration, about 100 ng to about 100 mg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 mg to about 10 mg per individual administration, about 1 mg to about 100 mg per individual administration, about 1 mg to about 1 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1 mg per individual administration, about 10 mg to about 10 mg per individual administration, about 10 mg to about 100 mg per individual administration, about 10 mg to about 1000 mg per injection, about 10 mg to about 10,000 mg per individual administration, about 100 mg to about 1 mg per individual administration, about 100 mg to about 10 mg per individual administration, about 100 mg to about 100 mg per individual administration, about 100 mg to about 1000 mg per injection, about 100 mg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The agent may be administered daily, every 2, 3, 4, 5, 6 or 7 days, or every 1, 2, 3 or 4 weeks.

In other particular embodiments, the amount of the EN3835 can be administered at a dose of about 0.0006 mg, 0.001 mg, 0.003 mg, 0.006 mg, 0.01 mg, 0.03 mg, 0.06 mg, 0.1 mg, 0.3 mg, 0.6 mg, 1 mg, 3 mg, 6 mg, 10 mg, 30 mg, 60 mg, 100 mg, 300 mg, 600 mg, 1000 mg, 2000 mg, 5000 mg or 10,000 mg. As expected, the dosage will be dependent on the condition, size, age and condition of the patient.

In certain embodiments, the coding sequences for a EN3835 is incorporated into a suitable expression vector (e.g., viral or non-viral vector) for expressing an effective amount of the protease in patient. In certain embodiments comprising administration of e.g., one or more recombinant AAV (rAAV) viruses, the pharmaceutical composition may comprise the rAAVs in an amount comprising at least $10^{10}$, at least $10^{11}$, at least $10^{12}$, at least $10^{13}$, or at least $10^{14}$ genome copies (GC) or recombinant viral particles per kg, or any range thereof. In certain embodiments, the pharmaceutical composition comprises an effective amount of the recombinant virus, such as rAAV, in an amount comprising at least $10^{10}$, at least $10^{11}$, at least $10^{12}$, at least $10^{13}$, at least $10^{14}$, at least $10^{15}$ genome copies or recombinant viral particles genome copies per subject, or any range thereof.

Dosages can be tested in several art-accepted animal models suitable for any particular cell proliferative disorder.

Delivery methodologies may also include the use of polycationic condensed DNA linked or unlinked to killed viruses, ligand linked DNA, liposomes, eukaryotic cell delivery vehicles cells, deposition of photopolymerized hydrogel materials, use of a handheld gene transfer particle gun, ionizing radiation, nucleic charge neutralization or fusion with cell membranes, particle mediated gene transfer and the like.

In other aspects of this embodiment, a pharmaceutical composition disclosed herein reduces the size of a stenotic area by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a pharmaceutical composition disclosed herein reduces the size of a stenotic area from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In other aspects of this embodiment, a pharmaceutical composition disclosed herein improves the signs/symptoms of bladder dysfunction by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a pharmaceutical composition disclosed herein improves the signs/symptoms of bladder dysfunction from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In other aspects of this embodiment, a pharmaceutical composition disclosed herein reduces the size of a region of prostate tissue by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a pharmaceutical composition disclosed herein reduces the size of a region of prostate tissue by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition disclosed herein is in an amount sufficient to allow customary administration to an individual. In aspects of this embodiment, a pharmaceutical composition disclosed herein can be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a pharmaceutical composition. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a pharmaceutical composition. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein can comprise a solvent, emulsion or other diluent in an amount sufficient to dissolve a pharmaceutical composition disclosed herein. In other aspects of this embodiment, a pharmaceutical composition disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent, emulsion or other diluent in an amount in a range of, e.g., about 1% (v/v) to about 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a pharmaceutical composition disclosed herein in a pharmaceutical composition disclosed herein can be of any concentration desired. In an aspect of this embodiment, the final concentration of a pharmaceutical composition in a pharmaceutical composition may be a therapeutically effective amount. In other aspects of this embodiment, the final concentration of a pharmaceutical composition in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL or at least 500 mg/mL. In other aspects of this embodiment, the final concentration of a pharmaceutical composition in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

Aspects of the present specification disclose, in part, treating an individual suffering from BPH, bladder dysfunction, tracheal stenosis, subglottic stenosis, esophageal stricture or scleroderma. As used herein, the term "treating," refers to reducing or eliminating in an individual a clinical symptom of stenosis; or delaying or preventing in an individual the onset of a clinical symptom of stenosis. For example, the term "treating" can mean reducing a symptom of a condition characterized by a stenosis, including, but not limited to, stenotic area size, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with bladder dysfunction, tracheal stenosis, subglottic stenosis, esophageal stricture or scleroderma are well known and can be determined by a person of ordinary skill in the art by taking into account factors, including, without limitation, the location of the stenosis, the cause, the severity, and/or the tissue or organ affected by the stenosis. Those of skill in the art will know the appropriate symptoms or indicators associated with a specific type of ailment and will know how to determine if an individual is a candidate for treatment as disclosed herein.

Similarly, the term "treating" can mean reducing a symptom of a condition characterized by an enlarged prostate, including, but not limited to, prostate size, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with enlarged prostate are well known and can be determined by a person of ordinary skill in the art by taking into account factors, including, without limitation, the cause, the severity, and/or effects of enlarged prostate. Those of skill in the art will know the appropriate symptoms or indicators associated with a specific type of ailment and will know how to determine if an individual is a candidate for treatment as disclosed herein.

In another aspect, a pharmaceutical composition disclosed herein reduces the severity of a symptom of a disorder associated with bladder dysfunction, tracheal stenosis, subglottic stenosis, esophageal stricture or scleroderma. In aspects of this embodiment, a pharmaceutical composition disclosed herein reduces the severity of a symptom of a disorder associated with bladder dysfunction, tracheal stenosis, subglottic stenosis, esophageal stricture or scleroderma by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a pharmaceutical composition disclosed herein reduces the severity of a symptom of a disorder associated with a stenosis or increase in collagen by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In aspects of this embodiment, a therapeutically effective amount of a pharmaceutical composition disclosed herein reduces a symptom associated with bladder dysfunction, BPH, tracheal stenosis, subglottic stenosis, esophageal stricture or scleroderma by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a pharmaceutical composition disclosed herein reduces a symptom associated with bladder dysfunction, BPH, tracheal stenosis, subglottic stenosis, esophageal stricture or scleroderma by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a pharmaceutical composition disclosed herein reduces a symptom associated with bladder dysfunction, BPH, tracheal stenosis, subglottic stenosis, esophageal stricture or scleroderma by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a pharmaceutical composition disclosed herein generally is in the range of about 0.001 mg/kg to about 100 mg/kg and administered, for example, every 3, 5, 7, 10 or 14 days. In aspects of this embodiment, an effective amount of a pharmaceutical composition disclosed herein may be, e.g., at least 0.001 mg/kg, at least 0.01 mg/kg, at least 0.1 mg/kg, at least 1.0 mg/kg, at least 5.0 mg/kg, at least 10 mg/kg, at least 15 mg/kg, at least 20 mg/kg, at least 25 mg/kg, at least 30 mg/kg, at least 35 mg/kg, at least 40 mg/kg, at least 45 mg/kg, or at least 50 mg/kg and administered, for example, every 3, 5, 7, 10 or 14 days. In other aspects of this embodiment, an effective amount of a pharmaceutical composition disclosed herein may be in the range of, e.g., about 0.001 mg/kg to about 10 mg/kg, about 0.001 mg/kg/day to about 15 mg/kg, about 0.001 mg/kg to about 20 mg/kg, about 0.001 mg/kg to about 25 mg/kg, about 0.001 mg/kg to about 30 mg/kg, about 0.001 mg/kg to about 35 mg/kg, about 0.001 mg/kg to about 40 mg/kg, about 0.001 mg/kg to about 45 mg/kg, about 0.001 mg/kg to about 50 mg/kg, about 0.001 mg/kg to about 75 mg/kg, or about 0.001 mg/kg to about 100 mg/kg and administered, for example, every 3, 5, 7, 10 or 14 days. In yet other aspects of this embodiment, an effective amount of a pharmaceutical composition disclosed herein may be in the range of, e.g., about 0.01 mg/kg to about 10 mg/kg, about 0.01 mg/kg to about 15 mg/kg, about 0.01 mg/kg to about 20 mg/kg, about 0.01 mg/kg to about 25 mg/kg, about 0.01 mg/kg to about 30 mg/kg, about 0.01 mg/kg to about 35 mg/kg, about 0.01 mg/kg to about 40 mg/kg, about 0.01 mg/kg to about 45 mg/kg, about 0.01 mg/kg to about 50 mg/kg, about 0.01 mg/kg to about 75 mg/kg, or about 0.01 mg/kg to about 100 mg/kg and administered, for example, every 3, 5, 7, 10 or 14 days. In still other aspects of this embodiment, an effective amount of a pharmaceutical composition disclosed herein may be in the range of, e.g., about 0.1 mg/kg to about 10 mg/kg, about 0.1 mg/kg to about 15 mg/kg, about 0.1 mg/kg to about 20 mg/kg, about 0.1 mg/kg to about 25 mg/kg, about 0.1 mg/kg to about 30 mg/kg, about 0.1 mg/kg to about 35 mg/kg, about 0.1 mg/kg to about 40 mg/kg, about 0.1 mg/kg to about 45 mg/kg, about 0.1 mg/kg to about 50 mg/kg, about 0.1 mg/kg to about 75 mg/kg, or about 0.1 mg/kg to about 100 mg/kg and administered, for example, every 3, 5, 7, 10 or 14 days.

Dosing can be single dosage or cumulative (serial dosing), and can be readily determined by one skilled in the art. For instance, treatment of a BPH or stenosis can comprise a one-time administration of an effective dose of a pharmaceutical composition disclosed herein. Alternatively, treatment of BPH, tracheal stenosis, subglottic stenosis or scleroderma may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In one embodiment, a therapeutic disclosed herein is capable of reducing the number of scar cells (i.e. collagen) or the size of the stenotic area in an individual suffering from a stenosis by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, a tracheal stenosis, subglottic stenosis or scleroderma therapeutic is capable of reducing the number of scar cells (i.e. collagen) or stenotic area size in an individual by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In one embodiment, a therapeutic disclosed herein is capable of reducing the number of prostate cells or the size of the prostate in an individual suffering from a BPH by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, a prostate therapeutic is capable of reducing the number of prostate cells in an individual by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In a further embodiment, a bladder dysfunction, BPH, tracheal stenosis, subglottic stenosis, esophageal stricture or scleroderma therapeutic and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of a bladder dysfunction, BPH, tracheal stenosis, subglottic stenosis, esophageal stricture or scleroderma therapeutic is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects of this embodiment, a therapeutically effective amount of a therapeutic disclosed herein reduces a stenotic area in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic disclosed herein reduces or maintains a stenotic area in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic disclosed herein reduces a stenotic area size in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

EXAMPLES

The following non-limiting examples are provided for illustrative purposes only in order to facilitate a more complete understanding of representative embodiments now contemplated. These examples are intended to be a mere subset of all possible contexts in which the components of the formulation may be combined. Thus, these examples should not be construed to limit any of the embodiments described in the present specification, including those pertaining to the type and amounts of components of the formulation and/or methods and uses thereof

Example 1

Method of Treatment of Tracheal Stenosis using EN3835

In this example, a patient suffers from tracheal stenosis after prolonged placement of an endotracheal tube or tracheostomy. Scar tissue in the trachea may be apparent by examination. The patient may also experience symptoms such as wheezing, coughing or shortness of breath along with difficulty breathing. A high-pitched squeal coming from your lungs when inhaling.

The EN3835 is first reconstitution from the lyophilized powder using common techniques. Before use the vial is placed at room temperature for 15 to 60 minutes. The vial containing the cake of lyophilized powder should be intact and white in color. Aseptic techniques should be used when reconstituting in solution. An Accufill syringe (i.e. a syringe with a rack and pinion component) can be preferred for injection because scar tissue is dense and higher pressure may be necessary to inject the drug product. Alternatively, a conventional syringe with a large diameter syringe may suffice.

The reconstituted EN3835 solution can be kept at room temperature (20° to 25° C./68° to 77° F.) for up to one hour or refrigerated at 2° to 8° C. (36° to 46° F.) for up to four hours prior to administration. However, it should be allowed to reach ambient temperature before injection. The course of treatment is summarized below. However, a person having ordinary skill in the art of medicine would be able to determine, without undue experimentation, the appropriate dosages and routes of administration of the expression vector used in the novel methods of the disclosure Dose per Each Injection=0.07 mg
Injection Volume per Each Injection=0.3 mL
Number Injections per Each Treatment Session=12 injections
Dose (mg) per Each Treatment Session=0.84 mg (12 injections×0.07 mg)
Injection Volume (mL) per Each Treatment Session=3.6 mL (12 injections×0.3 mL)
Cumulative EFP Dose=2.52 mg (3 treatment sessions× 0.84 mg)

In this example, the solution is injected at 12 sites at or near the stenosis. Because EN3835 acts locally at the site of injection, systemic exposure is not required for drug effectiveness. The area of the stenosis is monitored during the course of treatment. As can be appreciated, the treatment regime can be altered and/or extended based on the results.

Example 2

Method of Treatment of Subglottic Stenosis using EN3835

In this example, a patient presents signs and/or symptoms of subglottic stenosis. A diagnosis of subglottic stenosis may rely on clinical findings based on a thickening of an area or region in the trachea. Signs of Subglottic Stenosis include noisy breathing (stridor), respiratory distress, recurring croup and inability to breathe without a tracheostomy tube.

As described above, The EN3835 is first reconstitution from the lyophilized powder using common techniques. An Accufill syringe can used to inject the protease. The protease solution is injected at 12 sites at or near the stenosis. The course of treatment can be the same as described above. One or more subsequent injections can follow the initial injection. The area of the stenosis can be monitored during the course of treatment.

Example 3

Method of Treatment of Scleroderma using EN3835

In this example, a patient presents signs and/or symptoms of Scleroderma. Scleroderma, or systemic sclerosis, is a chronic connective tissue disease generally classified as one of the autoimmune rheumatic diseases. Hardening of the skin is one of the most visible manifestations of the disease. The thickened skin can involve scarring, blood vessel problems, varying degrees of inflammation and pain. In this example, the patient experiences strictures of the esophagus. Common symptoms include difficulty swallowing and discomfort with swallowing.

As described above, The EN3835 is first reconstitution from the lyophilized powder using common techniques. An Accufill syringe can be used to inject the protease. The course of treatment is summarized below.

Dose per Each Injection=0.035 mg
Injection Volume per Each Injection=0.15 mL
Number Injections per Each Treatment Session=12 injections
Dose (mg) per Each Treatment Session=0.42 mg (12 injections×0.035 mg)
Injection Volume (mL) per Each Treatment Session=3.6 mL (12 injections×0.3 mL)
Cumulative EFP Dose=1.26 mg (3 treatment sessions× 0.42 mg)

In this example, the solution is injected at 12 sites or near the stenotic region of the esophagus. One or more subsequent injections can follow the initial injection. The area of the stenosis can be monitored during the course of treatment.

Example 4

Method of Treatment of Benign Prostatic Hyperplasia (BPH) using EN3835

In this example, a male patient, age 80, presents common signs and symptoms of BPH. Specifically, he complains of difficulty urinating with a weak urinary stream and the inability to completely empty his bladder. A health care provider confirms BPH upon physical examination, blood and imaging tests and a urine flow study. The provider recommends EN3835 to break up to enlarged prostate tissue.

As described above, the EN3835 is first reconstitution from the lyophilized powder using common techniques. An Accufill syringe can be used to inject the protease. The course of treatment is summarized below.

Dose per Each Injection=0.035 mg
Injection Volume per Each Injection=0.15 mL
Number Injections per Each Treatment Session=6 injections
Dose (mg) per Each Treatment Session=0.42 mg (12 injections×0.035 mg)
Injection Volume (mL) per Each Treatment Session=1.8 mL (6 injections×0.3 mL)
Cumulative EFP Dose=1.26 mg (3 treatment sessions× 0.42 mg)

In this example, the solution is injected at six sites or near the prostate. Two subsequent treatment sessions follow the initial session. At each treatment session, injections are performed substantially the same. The size of the prostate can be monitored during the course of treatment.

Example 5

Method of Treatment of Esophageal Stricture

Strictures can form after esophageal surgery from scar tissue, causing the tissue to pull and tighten. In this example, a male patient, age 50, presents common signs and symptoms of esophageal stricture. Specifically, the patient complains of heartburn, chest pain, difficulty swallowing and a chronic cough. Further, the patient describes a history of GERD. A physician confirms the presence of strictures by endoscopy followed by an X-ray conducted while the patient swallowed barium (i.e., barium study of the esophagus). The provider recommends collagenase Clostridium histolyticum (CCH) to remove tissue from the stricture.

As described above, the CCH is first reconstitution from the lyophilized powder using common techniques. An Accufill syringe can be used to inject the CCH. The course of treatment is summarized below.

Dose per Each Injection=0.035 mg
Injection Volume per Each Injection=0.15 mL
Number Injections per Each Treatment Session=6 injections
Dose (mg) per Each Treatment Session=0.42 mg (12 injections×0.035 mg)
Injection Volume (mL) per Each Treatment Session=0.9 mL (6 injections×0.15 mL)
Cumulative EFP Dose=1.26 mg (3 treatment sessions× 0.42 mg)

In this example, the solution is injected at six sites or near the strictures. Two subsequent treatment sessions follow the initial session. At each treatment session, injections are performed substantially the same. The area of the strictures can be monitored during the course of treatment.

The use of CCH presents an alternative to conventional dilation techniques thus avoiding complications such as esophageal perforation. However, as described above, CCH can be used in conjunction with dilation techniques. For example, a health care provider can use a dilator (e.g., a mechanical or a balloon dilator) to physically stretch a stenotic region during a course of CCH injections. In this example, the physician also recommends a treatment plan for GERD to prevent strictures from returning.

Example 6

Method of Treating Urinary Incontinence

The detrusor muscle contracts during urination to push the urine out of the bladder and into the urethra. The detrusor muscle will relax to allow the storage of urine in the urinary bladder. Patients with urinary incontinence can have increased detrusor collagen content leading to decreased bladder compliance, detrusor overactivity, and urinary retention. In this example, a female patient, age 75, presents common signs and symptoms of urinary incontinence. Specifically, she complains of difficulty urinating with a weak urinary stream, the inability to completely empty her bladder and a leaky bladder. A health care provider conducts a physical examination, blood and imaging tests and a urine flow study. The provider recommends EN3835 to dissolve excess collagen in and near the bladder and detrusor muscle.

As described above, the EN3835 is first reconstitution from the lyophilized powder using common techniques. An Accufill syringe can be used to inject the CCH. The course of treatment is summarized below.

Dose per Each Injection=0.035 mg
Injection Volume per Each Injection=0.15 mL
Number Injections per Each Treatment Session=6 injections
Dose (mg) per Each Treatment Session=0.42 mg (12 injections×0.035 mg)
Injection Volume (mL) per Each Treatment Session=0.9 mL (6 injections×0.15 mL)
Cumulative EFP Dose=1.26 mg (3 treatment sessions× 0.42 mg)

In this example, the solution is injected at six sites around the detrusor muscle. Two subsequent treatment sessions follow the initial session. At each treatment session, injections are performed substantially the same. The signs/symptoms of urinary continence can be monitored during the course of treatment.

Example 7

Method of Treating Urinary Retention

Decreased bladder compliance can be considered a sign of bladder decompensation. Studies have demonstrated that increased detrusor collagen deposition can lead to a reduction of bladder compliance. Applicant avers that collagen deposition increases as bladder compliance decreases which supports the theory that the extracellular matrix components are important to viscoelastic properties of the bladder wall.

In this example, a male patient, age 65, presents common signs and symptoms of urinary retention. Specifically, he complains of difficulty urinating with a weak urinary stream, the inability to completely empty his bladder and abdominal pain. Previous treatments, including a catheter inserted through the urethra to decrease the size of the urethral dilation were unsuccessful. A health care provider conducts a physical examination, blood and imaging tests and a urine flow study. The provider recommends EN3835 to dissolve excess collagen in and near the bladder wall and detrusor muscle.

As described above, the EN3835 is first reconstitution from the lyophilized powder using common techniques. An Accufill syringe can be used to inject the protease. The course of treatment is summarized below.

Dose per Each Injection=0.035 mg
Injection Volume per Each Injection=0.15 mL
Number Injections per Each Treatment Session=6 injections
Dose (mg) per Each Treatment Session=0.42 mg (12 injections×0.035 mg)
Injection Volume (mL) per Each Treatment Session=0.9 mL (6 injections×0.15 mL)
Cumulative EFP Dose=1.26 mg (3 treatment sessions× 0.42 mg)

In this example, the solution is injected at six sites around the detrusor muscle. Two subsequent treatment sessions follow the initial session. At each treatment session, injections are performed substantially the same. The signs/symptoms of urinary retention can be monitored during the course of treatment.

Example 8

Method of Treating Bladder Obstruction

Urinary tract obstruction is a urologic disease that can cause urinary retention. Benign prostatic hyperplasia (BPH), also called prostate enlargement, is a noncancerous increase in size of the prostate gland. Symptoms can include frequent urination, trouble starting to urinate, weak stream, inability to urinate, or loss of bladder control. Complications can include urinary tract infections, bladder stones, and chronic kidney problems In this example, a male patient, age 70, presents common signs and symptoms of urinary retention. A health care provider conducts a physical examination, blood and imaging tests and a urine flow study. The health care provider recognizes that an enlarged prostate is obstructing the flow of urine. Further. The bladder wall and detrusor muscle have higher than normal levels of collagen. The provider recommends injecting CCH to reduce the size of the prostate, to improve bladder compliance and to improve action of the detrusor muscle.

As described above, the EN3835 is first reconstitution from the lyophilized powder using common techniques. An Accufill syringe can be used to inject the protease. The course of treatment is summarized below.

Dose per Each Injection=0.035 mg
Injection Volume per Each Injection=0.15 mL
Number Injections per Each Treatment Session=12 injections
Dose (mg) per Each Treatment Session=0.42 mg (12 injections×0.035 mg)
Injection Volume (mL) per Treatment Session=1.8 mL (12 injections×0.15 mL)
Cumulative EFP Dose=1.26 mg (3 treatment sessions× 0.42 mg)

In this example, the solution is injected at multiple sites at or near each of the prostate, the bladder wall and the detrusor muscle. Two subsequent treatment sessions follow the initial session. At each treatment session, injections are performed substantially the same. The signs/symptoms of urinary retention can be monitored during the course of treatment.

The therapeutic method of the present specification can include the step of administering drug product (i.e., EN3835) at a pharmaceutically effective amount. The total daily dose should be determined through appropriate medical judgment by a physician and administered once or several times. The specific therapeutically effective dose level for any particular patient may vary depending on various factors well known in the medical art, including the kind and degree of the response to be achieved, concrete compositions according to whether other agents are used therewith or not, the patient's age, body weight, health condition, gender, and diet, the time and route of administration, the secretion rate of the composition, the time period of therapy, other drugs used in combination or coincident with the composition disclosed herein, and like factors well known in the medical arts.

In still another aspect, the present specification provides a use of the therapeutic protein or the pharmaceutical composition including the same in the preparation of drugs for the prevention or treatment of BPH, tracheal stenosis, subglottic stenosis or scleroderma.

In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.01 mg/kg, at least 0.25 mg/kg, at least 0.3 mg/kg, at least 0.5 mg/kg, at least 0.75 mg/kg, at least 1 mg/kg, at least 2 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 15 mg/kg, at least 20 mg/kg, at least 25 mg/kg, or at least 30 mg/kg In one embodiment, a weekly dose may be at most 1.5 mg/kg, at most 2 mg/kg, at most 2.5 mg/kg, at most 3 mg/kg, at most 4 mg/kg, at most 5 mg/kg, at most 6 mg/kg, at most 7 mg/kg, at most 8 mg/kg, at most 9 mg/kg, at most 10 mg/kg, at most 15 mg/kg, at most 20 mg/kg, at most 25 mg/kg, or at most 30 mg/kg. In a particular aspect, the weekly dose may range from 5 mg/kg to 20 mg/kg. In an alternative aspect, the weekly dose may range from 10 mg/kg to 15 mg/kg.

The present specification also provides a pharmaceutical composition for the administration to a subject. The pharmaceutical composition disclosed herein may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition disclosed herein, and other factors known in medicine.

The pharmaceutical composition including the protease disclosed herein may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition disclosed herein may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

The composition may be formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition disclosed herein are determined by the type of active ingredient, together with various factors such as the disease to be treated, administration route, patient's age, gender, and body weight, and disease severity.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the peptide disclosed herein may be approximately 0.0001 µg to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects.

Moreover, the pharmaceutical composition may be administered alone or in combination or coincident with other pharmaceutical formulations showing prophylactic or therapeutic efficacy.

Given the teachings and guidance provided herein, those skilled in the art will understand that a formulation described herein can be equally applicable to many types of biopharmaceuticals, including those exemplified, as well as others known in the art. Given the teachings and guidance provided herein, those skilled in the art also will understand that the selection of, for example, type(s) or and/or amount(s) of one or more excipients, surfactants and/or optional components can be made based on the chemical and functional compatibility with the biopharmaceutical to be formulated and/or the mode of administration as well as other chemical, functional, physiological and/or medical factors well known in the art. For example, non-reducing sugars exhibit favorable excipient properties when used with polypeptide biopharmaceuticals compared to reducing sugars. Accordingly, exemplary formulations are exemplified further herein with reference to polypeptide biopharmaceuticals. However, the range of applicability, chemical and physical properties, considerations and methodology applied to polypeptide biopharmaceutical can be similarly applicable to biopharmaceuticals other than polypeptide biopharmaceuticals.

In various embodiments, a formulation can include, without limitation, combinations of bioactive agents (such as viruses, proteins, antibodies, peptides and the like as described herein) in the formulation. For example, a formulation as described herein can include a single bioactive agent for treatment of one or more conditions. A formulation as described herein also can include, in an embodiment, two or more different bioactive agents for a single or multiple conditions. Use of multiple bioactive agents in a formulation can be directed to, for example, the same or different indications. Similarly, in another embodiment, multiple bioactive agents can be used in a formulation to treat, for example, both a pathological condition and one or more side effects caused by the primary treatment. In a further embodiment, multiple bioactive agents also can be included, in a formulation as described herein to accomplish different medical purposes including, for example, simultaneous treatment and monitoring of the progression of the pathological condition. In an additional embodiment, multiple, concurrent therapies such as those exemplified herein as well as other combinations well known in the art are particularly useful for patient compliance because a single formulation can be sufficient for some or all suggested treatments and/or diagnosis. Those skilled in the art will know those bioactive agents that can be admixed for a wide range of combination therapies. Similarly, in various embodiments, a formulation can be used with a small molecule drug and combinations of one or more bioactive agents together with one or more small molecule pharmaceuticals. Therefore, in various embodiments a formulation is provided containing 1, 2, 3, 4, 5 or 6 or more different bioactive agents, as well as, for one or more bioactive agents combined with one or more small molecule pharmaceuticals.

In various embodiments, a formulation can include, one or more preservatives and/or additives known in the art. Similarly, a formulation can further be formulated, without limitation, into any of various known delivery formulations. For example, in an embodiment, a formulation can include, surfactants, adjuvant, biodegradable polymers, hydrogels, etc., such optional components, their chemical and functional characteristics are known in the art. Similarly known in the art are formulations that facilitate rapid, sustained or delayed release of the bioactive agents after administration. A formulation as described can be produced to include these or other formulation components known in the art.

The composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In various embodiments, the bioactive agents in formulations described herein can, without limitation, be administered to patients throughout an extended time period, such as chronic administration for a chronic condition. The composition can be a solid, a semi-solid or an aerosol and a pharmaceutical compositions is formulated as a tablet, geltab, lozenge, orally dissolved strip, capsule, syrup, oral suspension, emulsion, granule, sprinkle or pellet.

The doses of the collagenase *Clostridium histolyticum* can be expressed in mg per injection such as from about 0.001 mg to 0.5 mg per injection, about 0.01 mg to about 5 mg per injection, or about 0.005 mg to about 0.1 mg, or about 0.005 mg, 0.04 mg, or 0.07 mg per injection. The collagenase mixture may be in the form of a pharmaceutical formulation comprising the collagenase and pharmaceutically acceptable excipients.

For example, about 0.84 mg of collagenase *Clostridium histolyticum* can be administered in 12 equally divided injections to an affected area every 15-25 days totaling a dose of about 0.84 mg per treatment session (i.e. 0.07 mg×12 injections=0.84 mg). Collagenases other than EN3835 that may also be suitable are described, for example, in U.S. Pat. Nos. 7,811,560; 9,757,435; 9,744,138; and WO2012/125948.

The doses of the collagenase *Clostridium histolyticum* can be expressed in units per injection. For example, EN3835 can have a specific activity of about 10,000 ABC units/mg to about 25,000 ABC units/mg, or about 15,000 ABC units/mg, or about 17,500 ABC units/mg, or about 20,000 ABC units/mg, or about 22,500 ABC units/mg, or about 10,000 ABC units/0.58 mg, or 17,241 ABC units/mg wherein "mg" refers to the amount of collagenase(s) present in a composition (as distinct from excipients and other constituents). Accordingly, the present invention contemplates injecting about 500 ABC units to about 50,000 ABC units per treatment session, or about 10,000 ABC units to about 25,000 ABC units per treatment session.

In another embodiment, the dose of collagenase per injection is about 50 ABC units to about 2,500 ABC units, or about 85 ABC units to about 2,000 ABC units, or about 150 ABC units to about 1,750 ABC units, or about 200 ABC units to about 1,500 ABC units, or about 300 ABC units to about 1,250 ABC units, or about 500 ABC units to about 1,000 ABC units.

Packaging and instruments for administration may be determined by a variety of considerations, such as, without limitation, the volume of material to be administered, the conditions for storage, whether skilled healthcare practitioners will administer or patient self-compliance, the dosage regime, the geopolitical environment (e.g., exposure to extreme conditions of temperature for developing nations), and other practical considerations.

Injection devices include pen injectors, auto injectors, safety syringes, injection pumps, infusion pumps, glass prefilled syringes, plastic prefilled syringes and needle free injectors syringes may be prefilled with liquid, or may be dual chambered, for example, for use with lyophilized material. An example of a syringe for such use is the Lyo-Ject™, a dual-chamber pre-filled lyosyringe available from Vetter GmbH, Ravensburg, Germany. Another example is the LyoTip which is a prefilled syringe designed to conveniently deliver lyophilized formulations available from LyoTip, Inc., Camarillo, Calif., U.S.A. Administration by injection may be, without limitation intravenous, intramuscular, intraperitoneal, or subcutaneous, as appropriate. Administrations by non-injection route may be, without limitation, nasal, oral, cocular, dermal, or pulmonary, as appropriate.

In certain embodiments, kits can comprise, without limitation, one or more single or multi-chambered syringes (e.g., liquid syringes and lyosyringes) for administering one or more formulations described herein. In various embodiments, the kit can comprise formulation components for parenteral, subcutaneous, intramuscular or IV administration, sealed in a vial under partial vacuum in a form ready for loading into a syringe and administration to a subject. In this regard, the composition can be disposed therein under partial vacuum. In all of these embodiments and others, the kits can contain one or more vials in accordance with any of the foregoing, wherein each vial contains a single unit dose for administration to a subject.

The kits can comprise lyophilates, disposed as herein, that upon reconstitution provide compositions in accordance therewith. In various embodiment the kits can contain a lyophilate and a sterile diluent for reconstituting the lyophilate.

Also described herein, are methods for treating a subject in need of therapy, comprising administering to the subject an effective amount of a formulation as described herein. The therapeutically effective amount or dose of a formulation will depend on the disease or condition of the subject and actual clinical setting.

In an embodiment, a formulation as described herein can be administered by any suitable route, specifically by parental (including subcutaneous, intramuscular, intravenous and intradermal) administration. It will also be appreciated that the preferred route will vary with the condition and age of the recipient, and the disease being treated. Methods of determining the most effective means and dosage of administration are known to those of skill in the art and will vary, without limitation, with the composition used for therapy, the purpose of the therapy, and the subject being treated. Single or multiple administrations can be carried out, without limitation, the dose level and pattern being selected by the treating physician. Suitable dosage formulations and methods of administering the agents are known in the art.

The formulations as described herein can be used in the manufacture of medicaments and for the treatment of humans and other animals by administration in accordance with conventional procedures.

Also provided herein are combinatorial methods for developing suitable virus formulations using combinations of amino acids. These methods are effective for developing stable liquid or lyophilized formulations, and particularly pharmaceutical virus formulations.

Compositions in accordance with embodiments described herein have desirable properties, such as desirable solubility, viscosity, syringeability and stability. Lyophilates in accordance with embodiments described herein have desirable properties, as well, such as desirable recovery, stability and reconstitution.

In an embodiment, the pH of the pharmaceutical formulation is at least about 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, or 9.

In an embodiment, the pH of the pharmaceutical formulation is from about 3 to about 9, about 4 to about 19, about 5 to about 9, about 6 to about 8, about 6 to about 7, about 6 to about 9, about 5 to about 6, about 5 to about 7, about 5 to about 8, about 4 to about 9, about 4 to about 8, about 4 to about 7, about 4 to about 6, about 4 to about 5, about 3 to about 8, about 3 to about 7, about 3 to about 6, about 3 to about 5, about 3 to about 4, about 7 to about 8, about 7 to about 9, about 7 to about 10.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A method of treating a patient with bladder dysfunction comprising injecting an effective amount of collagenase from *Clostridium histolyticum* at or near the bladder an/or the detrusor muscle of the bladder.

2. The method of claim 1, wherein the bladder dysfunction causes one or more of urinary incontinence and urinary retention.

3. The method of claim 1, wherein the injecting comprises multiple injections at a plurality of sites at or near the bladder and/or the detrusor muscle of the bladder.

4. The method of claim 3, wherein each of the multiple injections is comprised of a volume of about 0.2 ml or less.

5. The method of claim 1, wherein a total of 0.01 mg to 0.5 mg of collagenase in solution is injected.

6. The method of claim 1, wherein a total of 0.02 mg to 0.05 mg of collagenase in solution is injected.

7. The method of claim 1, including an additional step of endoscopic dilation.

8. The method of claim 1, wherein the collagenase is comprised of equal amounts of Clostridial class I collagenase (AUX-I) and Clostridial class II collagenase (AUX-II).

9. The method of claim 1, wherein the collagenase is injected using a syringe with a rack and pinion component.

10. A method of treating bladder dysfunction in a patient comprising steps of:
 a) identifying a patient with signs and/or symptoms of bladder dysfunction,
 b) injecting an effective amount of collagenase from *Clostridium histolyticum* at a first plurality of sites at or near the bladder and/or the detrusor muscle of the bladder,
 c) monitoring signs and/or symptoms of bladder dysfunction,
 d) injecting an effective amount of collagenase at a second plurality of sites at or near the bladder and/or the detrusor muscle of the bladder, and
 e) repeating steps c) and d) until the signs and/or symptoms of bladder dysfunction subside,
 wherein the bladder dysfunction causes one or more of urinary incontinence and urinary retention.

11. The method of claim 10, wherein each injection has a volume of about 0.2 ml or less.

12. The method of claim 10, wherein a total of 0.01 mg to 0.5 mg of collagenase in solution is injected.

13. The method of claim 10, wherein a total of 0.02 mg to 0.05 mg of collagenase in solution is injected.

14. The method of claim 10, including an additional step of endoscopic dilation.

15. The method of claim 10, wherein the collagenase is comprised of equal amounts of Clostridial class I collagenase (AUX-I) and Clostridial class II collagenase (AUX-II).

16. The method of claim 10, wherein the collagenase is injected using a syringe with a rack and pinion component.

17. A method of treating a patient with bladder obstruction comprising injecting an effective amount of collagenase from *Clostridium histolyticum* at or near one or more of:
 a) the bladder of the patient,
 b) the detrusor muscle of the patient, and
 c) the prostate of the patient.

18. The method of claim 17, wherein each injection has a volume of about 0.2 ml or less.

19. The method of claim 17, wherein the collagenase is comprised of equal amounts of Clostridial class I collagenase (AUX-I) and Clostridial class II collagenase (AUX-II).

20. The method of claim 17, wherein the collagenase is injected using a syringe with a rack and pinion component.

* * * * *